(12) United States Patent
Gregorius et al.

(10) Patent No.: US 6,262,286 B1
(45) Date of Patent: Jul. 17, 2001

(54) METHOD FOR SELECTIVE PRODUCTION OF RACEMIC METALLOCENE COMPLEXES

(75) Inventors: Heike Gregorius, Bad Kreuznach; Carsten Süling, Frankenthal; Wolfgang Bidell, Mutterstadt; Hans-Herbert Brintzinger, Taegerswilen; Hans-Robert-Hellmuth Damrau, Konstanz; Armin Weber, Markdorf, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,970
(22) PCT Filed: Sep. 17, 1998
(86) PCT No.: PCT/EP98/05918
§ 371 Date: Mar. 20, 2000
§ 102(e) Date: Mar. 20, 2000
(87) PCT Pub. No.: WO99/15538
PCT Pub. Date: Apr. 1, 1999

(30) Foreign Application Priority Data

Sep. 23, 1997 (DE) .............................................. 197 41 876

(51) Int. Cl.$^7$ .............................. C07F 17/00; B01J 31/00; C08F 4/64
(52) U.S. Cl. .................................. 556/11; 556/12; 556/1; 556/43; 556/53; 556/58; 526/126; 526/160; 526/943; 502/103; 502/117; 502/153
(58) Field of Search ................................... 556/11, 12, 43, 556/54, 58, 1; 502/103, 117, 153; 526/126, 160, 943

(56) References Cited

U.S. PATENT DOCUMENTS 5,840,950  11/1998  Fischer et al. ......................... 556/11

FOREIGN PATENT DOCUMENTS 195 25 184   1/1997   (DE) .
92/09545     6/1992   (WO) .

OTHER PUBLICATIONS

J.Org.Met.Chem.,497(1995) 133–142, Kuntz.
XP–002089633,Chem.Ltrs., 383–384, Habaue et al.
Organometallics 1997,16,1724–1728, Schmidt et al.
J.Org.Chem.,415 (1991) 75–85,Erickson et al.
J.Org.Chem.,232 (1982) 233–247, Wild et al.
J.Am.Chem.Soc.1991,113,6270–6271,Coates et al.
J.Am.Chem.Soc.1990,112,4911–4914,Waymouth et al.
Angew.Chem.101 (1989) Nr.9, Kaminsky et al.

Primary Examiner—Porfirio Nazario-Gonzalez
(74) Attorney, Agent, or Firm—Keil & Weinkauf

(57) ABSTRACT

Racemic metallocene complexes are prepared by reacting bridged or unbridged transition metal complexes with cyclopentadienyl derivatives of alkali metals or alkaline earth metals and, if desired, subsequently replacing the aromatic ligands.

10 Claims, No Drawings

METHOD FOR SELECTIVE PRODUCTION OF RACEMIC METALLOCENE COMPLEXES

The present invention relates to a process for preparing racemic metallocene complexes by reacting bridged or unbridged aromatic transition metal complexes of the formula I

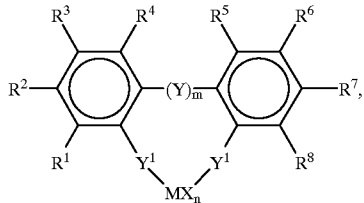

(I)

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen $C_1$–$C_{10}$-alkyl, $C_6$–$C_{15}$-aryl, alkylaryl having from 1 to 10 carbon atoms in the alkyl radical and from 6 to 20 carbon atoms in the aryl radical, —$OR^{10}$ or —$NR^{10}R^{11}$, n is an integer from 1 to 4, where n corresponds to the valence of M minus 2, $R^1$, $R^8$ are identical or different and are each fluorine, chlorine, bromine, iodine, $C_1$–$C_{20}$-alkyl, 3- to 8-membered cycloalkyl which in turn may bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, $R^2$ to $R^7$ are identical or different and are each hydrogen, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms, and the radicals mentioned can be fully or partially substituted by heteroatoms, $R^{10}$, $R^{11}$ are $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, $Y^1$ are identical or different and are each

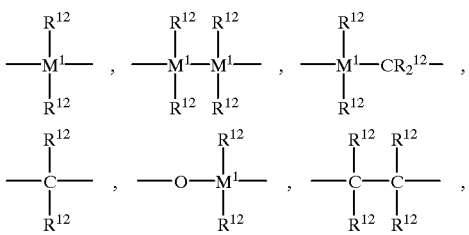

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2 or 3, or Y is non-bridging and is two radicals R' and R", where R' and R" are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms, with cyclopentadienyl derivatives of alkali metals or alkaline earth metals and, if desired, subsequently replacing the bridged aromatic ligand or the two unbridged aromatic ligands; racemic metallocene complexes of the formula III

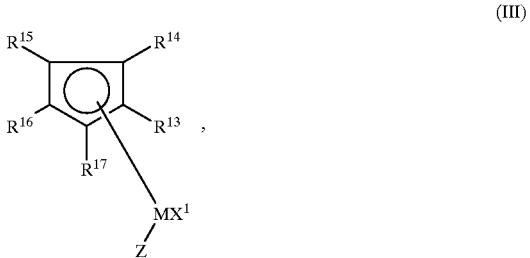

(III)

where the substituents and indices have the following meanings:

M is titanium, zirconium, hafnium, vanadium, niobium, tantalum, chromium, molybdenum, tungsten or an element of transition group III of the Periodic Table and of the lanthanides,

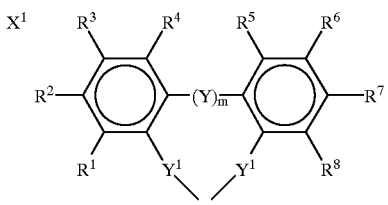

where:
- $R^1$, $R^8$ are identical or different and are each fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms,
- $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms and the radicals mentioned may be fully or partially substituted by heteroatoms,
- Y, $Y^1$ are identical or different and are each

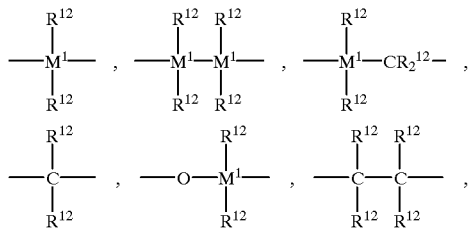

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where
- $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring,
- $M^1$ is silicon, germanium or tin and
- m is 0, 1, 2 or 3, or Y is non-bridging and is two radicals R' and R'', where
- R' and R'' are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms,
- $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where
- $R^{18}$ are identical or different and are each $C_1$–$C_{10}$-alkyl, $C_6$–$C_{15}$-aryl or $C_3$–$C_{10}$-cycloalkyl, Z is 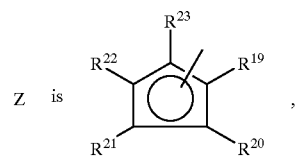, where the radicals
- $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where
- $R^{24}$ are identical or different and are each $C_1$–$C_{10}$-alkyl, $C_6$–$C_{15}$-aryl or $C_3$–$C_{10}$-cycloalkyl, or where the radicals
- $R^{16}$ and Z together form a group —$[T(R^{25})(R^{26})]_q$—E—, where
- T can be identical or different and are each silicon, germanium, tin or carbon,
- $R^{25}$, $R^{26}$ are each hydrogen, $C_1$–$C_{10}$-alkyl, $C_3$–$C_{10}$-cycloalkyl or $C_6$–$C_{15}$-aryl
- q is 1, 2, 3 or 4,
- E is

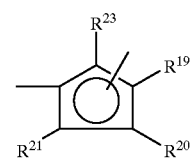

or A, where A is —O—,

where
- $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where
- $R^{28}$ are identical or different and are each $C_1$–$C_{10}$-alkyl, $C_6$–$C_{15}$-aryl, $C_3$–$C_{10}$-cycloalkyl or alkylaryl and the use of racemic metallocene complexes of the formula III as catalysts or as constituents of catalysts for the polymerization of olefinically unsaturated compounds or as reagents or as catalysts in stereoselective synthesis.

Apart from stereospecific olefin polymerization, enantioselective organic synthesis is increasingly providing interesting possibilities for using chiral metallocene complexes of metals of transition groups III–VI of the Periodic Table of the Elements. As an example, mention may be made here of enantioselective hydrogenations of prochiral substrates, for example prochiral olefins as described in R. Waymouth, P. Pino, J. Am. Chem. Soc. 112 (1990), pp. 4911–4914, or prochiral ketones, imines and oximes as described in WO 92/9545.

Furthermore, mention may be made of the preparation of optically active alkenes by enantioselective oligomerization as described in W. Kaminsky et al., Angew. Chem. 101 (1989), pp. 1304–1306, and enantioselective cyclopolymerization of 1,5-hexadienes as described in R. Waymouth, G. Coates, J. Am. Chem. Soc. 113 (1991), pp. 6270–6271.

The applications mentioned generally require the use of a metallocene complex in its racemic form, ie. without meso compounds. In the case of the diastereomer mixture (rac. and meso form) obtained in the metallocene synthesis of the prior art, the meso form has to be separated off first. Since the meso form has to be discarded, the yield of racemic metallocene complex is low.

It is an object of the present invention to find a process or the selective preparation of racemic, virtually (to the accuracy of NMR measurement) meso-free metallocene complexes.

A further object is to find racemic metallocene complexes which can either be used directly as or in catalysts, primarily for olefin polymerization, or which after modification, for example after substitution by an "auxiliary ligand", can be used as or in catalysts, primarily for olefin polymerization, or which can be used as reagents or catalysts in stereoselective synthesis.

We have found that these objects are achieved by the process defined in the claims, the racemic metallocene complexes III and their use as catalysts or in catalysts for the polymerization of olefinically unsaturated compounds or as reagents or as catalysts in stereoselective synthesis.

The terms "meso form", "racemate", and thus also "enantiomers" in relation to metallocene complexes are known and defined, for example, in Rheingold et al., Organometallics 11 (1992), pp. 1869–1876.

For the purposes of the present invention, the term "virtualy meso-free" means that at least 90% of a compound is present in the form of the racemate.

The bridged or unbridged aromatic transition metal complexes of the present invention have the formula I

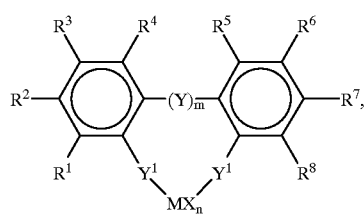

(I)

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen $C_1$–$C_{10}$-alkyl, $C_6$–$C_{15}$-aryl, alkylaryl having from 1 to 10 carbon atoms in the alkyl radical and from 6 to 20 carbon atoms in the aryl radical, —$OR^{10}$ or —$NR^{10}R^{11}$, n is an integer from 1 to 4, where n corresponds to the valence of M minus 2, $R^1$, $R^8$ are identical or different and are each fluorine, chlorine, bromine, iodine, $C_1$–$C_{20}$-alkyl, 3- to 8-membered cycloalkyl which in turn may bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, $R^2$ to $R^7$ are identical or different and are each hydrogen, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms, and the radicals mentioned can be fully or partially substituted by heteroatoms, $R^{10}$, $R^{11}$ are $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, $Y^1$ are identical or different and are each

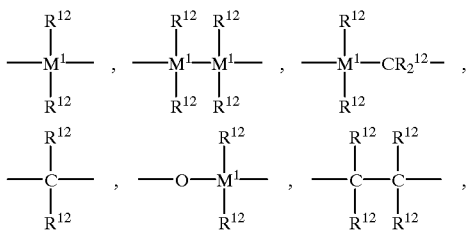

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2 or 3, or Y is non-bridging and is two radicals R' and R", where R' and R" are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms, Preferred metals M are titanium, zirconium and hafnium, in particular zirconium.

Well suited substituents X are fluorine, chlorine, bromine, iodine, preferably chlorine, also $C_1$–$C_6$-alkyl such as methyl, ethyl, n-propyl, iso-propyl, n-butyl, sec-butyl, i-butyl or preferably tert-butyl. Also well suited as substituents X are alkoxides —$OR^{10}$ or amides —$NR^{10}R^{11}$ where $R^{10}$ or $R^{11}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical. Such radicals X are, for example, methyl, ethyl, i-propyl, tert-butyl, phenyl, naphthyl, p-tolyl, benzyl, trifluoromethyl, pentafluorophenyl.

The substituents $R^1$ and $R^8$ are identical or different and are each fluorine, chlorine, bromine, iodine, $C_1$–$C_{20}$-alkyl, 3- to 8-membered cycloalkyl which may in turn bear a $C_1$–$C_{10}$-alkyl radical as substituent, e.g. methyl, ethyl or propyl. Examples of such cycloalkyl radicals are cyclopropyl, cyclopentyl, preferably cyclohexyl, norbornyl. The substituents $R^1$ and $R^8$ may also be $C_6$–$C_{15}$-aryl such as phenyl, naphthyl; alkylaryl having from 1 to 10 carbon atoms in the alkyl radical and from 6 to 20 carbon atoms in the aryl radical, e.g. p-tolyl; arylalkyl having from 1 to 10 carbon atoms in the alkyl radical and from 6 to 20 carbon atoms in the aryl radical, e.g. benzyl or neophyl, or they are triorganosilyl such as $Si(R^9)_3$ where $R^9$ are identical or different and are each $C_1$–$C_{20}$-alkyl, $C_3$–$C_{10}$-cycloalkyl, $C_6$–$C_{15}$-aryl, for example trimethylsilyl, tert-butyldimethylsilyl, triphenylsilyl. The radicals mentioned can, of course, also be partially or fully substituted by heteroatoms, for example by S—, N—, O—, or halogen-containing structural elements. Examples of such substituted radicals $R^1$ and $R^8$ are trifluoromethyl, pentafluoroethyl, heptafluoropropyl, heptafluoroisopropyl, pentafluorophenyl.

Preferred substituents $R^1$ and $R^8$ are those which take up a lot of space. Such substituents are usually called bulky substituents. They are distinguished by the fact that they can cause steric hindrance.

In general, these groups are organic or organosilicon radicals which take up a lot of space (bulky radicals), but also fluorine and preferably chlorine, bromine and iodine. The number of carbon atoms in such organic or organosilicon radicals is usually not less than three.

Preferred non-aromatic, bulky radicals are those organic or organosilicon radicals which are branched in the α position or a higher position. Examples of such radicals are branched $C_3$–$C_{20}$-aliphatic, $C_9$–$C_{20}$-araliphatic and $C_3$–$C_{10}$-cycloaliphatic radicals, e.g. iso-propyl, tert-butyl, iso-butyl, neo-pentyl, 2-methyl-2-phenylpropyl (neophyl), cyclohexyl, 1-methylcyclohexyl, bicyclo[2.2.1]hept-2-yl (2-norbornyl), bicyclo[2.2.1]hept-1-yl (1-norbornyl), adamantyl. Further possible radicals of this type are organosilicon radicals having from three to thirty carbon atoms, for example trimethylsilyl, triethylsilyl, triphenylsilyl, tert-butyldimethylsilyl, tritolylsilyl or bis(trimethylsilyl)methyl.

Preferred aromatic, bulky groups are, as a rule, $C_6$–$C_{20}$-aryl radicals such as phenyl, 1- or 2-naphthyl or preferably $C_1$–$C_{10}$-alkyl- or $C_3$–$C_{10}$-cycloalkyl-substituted aromatic radicals such as 2,6-dimethylphenyl, 2,6-di-tert-butylphenyl, mesityl.

Very particularly preferred substituents $R^1$ and $R^8$ are i-propyl, tert-butyl, trimethylsilyl, cyclohexyl, i-butyl, trifluoromethyl, 3,5-dimethylphenyl.

In the preferred substitution pattern, $R^1$ and $R^8$ in formula I are identical.

The substituents $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical such as methyl, ethyl or propyl as substituent. Examples of such cycloalkyl radicals are cyclopropyl, cyclopentyl, preferably cyclohexyl, norbornyl. Furthermore, the substituents $R^2$ to $R^7$ may be $C_6$–$C_{15}$-aryl, such as phenyl or naphthyl, alkylaryl having from 1 to 10 carbon atoms in the alkyl radical and from 6 to 20 carbon atoms in the aryl radical, e.g. p-tolyl, arylalkyl having from 1 to 10 carbon atoms in the alkyl radical and from 6 to 20 carbon atoms in the aryl radical, e.g. benzyl or neophyl, or they are triorganosilyl such as $Si(R^9)_3$ where $R^9$ are identical or different and are each $C_1$–$C_{20}$-alkyl, $C_3$–$C_{10}$-cycloalkyl or $C_6$–$C_{15}$-aryl, for example trimethylsilyl, tert-butyldimethylsilyl, triphenylsilyl. However, the radicals $R^2$ to $R^7$ can also be connected to one another in such a way that adjacent radicals form saturated, partially saturated or unsaturated cyclic groups having from 4 to 15 carbon atoms. Preferably, the radicals $R^3$ and $R^4$ and/or the radicals $R^5$ and $R^6$ are connected via a $C_2$-bridge in such a way that a benzo-fused ring system (naphthyl derivative) is formed. The radicals $R^2$ to $R^7$ can, of course, also be partially or fully substituted by heteroatoms, for example by S—, N—, O—, or halogen-containing structural elements. Examples of such substituted radicals $R^2$ to $R^7$ are trifluoromethyl, pentafluoroethyl, heptafluoropropyl, heptafluoroisopropyl, pentafluorophenyl.

Particularly preferably, the radicals $R^2$ and $R^7$ are identical and are each hydrogen and $R^3$, $R^4$, $R^5$ and $R^6$ are as defined above.

Suitable bridging units Y, $Y^1$ are the following:

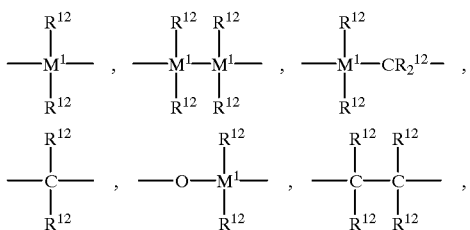

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where $R^{12}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$, in each case together with the atoms connecting them, form a ring, $M^1$ is silicon, germanium or tin.

Preferred bridging units Y, $Y^1$ are methylene —$CH_2$—, S, O, —$C(CH_3)2$—, where m in formula I is preferably 1 or 2; $Y^1$ are very particularly preferably identical and are each oxygen —O—. Very particular preference is given to phenoxide-type structures in which m in the formula I is zero, ie. the aromatic ring systems are linked directly to one another, for example to form a biphenyl derivative.

Among the unbridged aromatic transition metal complexes of the present invention of the formula I, preference is given to those in which Y represent radicals R' and R" which are identical or different and are fluorine, chlorine, bromide, iodine, $C_1-C_{20}$-alkyl or 3- to 8-membered cycloalkyl which may in turn bear a $C_1-C_{10}$-alkyl radical such as methyl, ethyl or propyl. Examples of such cycloalkyl radicals are cyclopropyl, cyclopentyl, preferably cyclohexyl, norbornyl. Further possible meanings of the substituents R' and R" are $C_6-C_{15}$-aryl such as phenyl or naphthyl; alkylaryl having from 1 to 10 carbon atoms in the alkyl radical and from 6 to 20 carbon atoms in the aryl radical, e.g. p-tolyl; arylalkyl having from 1 to 10 carbon atoms in the alkyl radical and from 6 to 20 carbon atoms in the aryl radical, e.g. benzyl or neophyl, or triorganosilyl such as $Si(R^9)_3$ where $R^9$ are identical or different and are each $C_1-C_{20}$-alkyl, $C_3-C_{10}$-cycloalkyl or $C_6-C_{15}$-aryl, for example trimethylsilyl, tert-butyldimethylsilyl or triphenylsilyl. The radicals mentioned can of course also be fully or partially substituted by heteroatoms, for example by structural elements containing S, N, O or halogen atoms. Examples of such substituted radicals R' and R" are the trifluoromethyl, pentafluoroethyl, heptafluoropropyl, heptafluoroisopropyl and pentafluorophenyl groups.

R' and R" are particularly preferably identical. Very particularly preferred unbridged aromatic transition metal complexes are ones in which $R^1$, $R^8$, R' and R" are identical.

The bridged or unbridged aromatic transition metal complexes I are generally prepared by methods with which those skilled in the art are familiar.

The synthesis of bridged transition metal phenoxide complexes is described for example in C. J. Schaverien, J. Am. Chem. Soc. (1995), pages 3008 to 3012. It has been found to be useful to employ the following procedure, which is generally carried out at from 0 to 80° C., preferably at first at about 20° C., and the reaction is then completed by boiling under reflux. The biphenol is first deprotonated in a solvent, for example tetrahydrofuran (THF), for example using sodium hydride or n-butyllithium, and the transition metal compound, for example the halide such as titanium tetrachloride, zirconium tetrachloride or hafnium tetrachloride, advantageously in the form of the bis-THF adducts, is subsequently added. After the reaction is complete, the product is generally obtained by crystallization after removal of salts. Unbridged transition metal phenoxide complexes can be prepared, for example, as described by H. Yasuda et al., J. Organomet. Chem. 473 (1994), pages 105 to 116.

The bridged or unbridged aromatic transition metal complexes I of the present invention generally still contain from 2 to 4 equivalents of a Lewis base which is generally introduced as a result of the synthetic route. Examples of such Lewis bases are ethers such as diethyl ether or tetrahydrofuran (THF). It is, however, also possible to obtain the aromatic transition metal complexes free of Lewis bases, for example by drying under reduced pressure or by selecting other solvents in the synthesis. Such measures are known to those skilled in the art.

The racemic metallocene complexes of the present invention are prepared by reacting the bridged or unbridged aromatic transition metal complexes I with cyclopentadienyl derivatives of the alkali metals or alkaline earth metals. Preference is given to using aromatic transition metal complexes I in which M is zirconium and the radicals $R^1$ and $R^8$ have the preferred meanings described above. Very useful aromatic transition metal complexes I are dichlorobis(6-tert-butyl-4-methylphenoxy)zirconium.(THF)$_2$ and the zirconium phenoxide compounds mentioned in the examples.

In principle, suitable cyclopentadienyl derivatives of the alkali metals or alkaline earth metals are those which, after reaction with the bridged aromatic transition metal complexes I of the present invention, selectively give virtually meso-free, racemic metallocene complexes.

The racemic metallocene complexes of the present invention may be bridged, but do not have to be. In general, a high barrier to rotation, in particular in the temperature range from 20 to 80° C., (which can be determined by $^1$H and/or $^{13}$C-NMR-spectroscopy) of the unbridged cyclopentadienyl-type ligands in the metallocene is sufficient to enable the metallocene complexes to be isolated directly in their racemic form without them being able to transform into the meso form. The barrier to rotation necessary to ensure this is usually above 20 kJ/mol.

Well suited cyclopentadiene derivatives of alkali metals or alkaline earth metals are those of the formula II

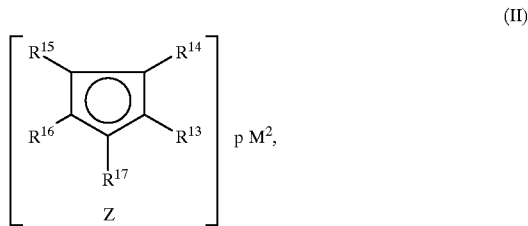

(II)

where the substituents and indices have the following meanings:

$M^2$ is Li, Na, K, Rb, Cs, Be, Mg, Ca, Sr, Ba, $R^{13}$ to $R^{17}$ are identical or different and are each hydrogen, $C_1-C_{20}$-alkyl, 5- to 7-membered cycloalkyl which may in turn bear a $C_1-C_{10}$-alkyl group as substituent, $C_6-C_{15}$-aryl or arylalkyl, where adjacent radicals may together form cyclic groups having from 4 to 15 carbon atoms, or $Si(R^{18})_3$ where $R^{18}$ are identical or different and are each $C_1-C_{10}$-alkyl, $C_6-C_{15}$-aryl or $C_3-C_{10}$-cycloalkyl, Z is 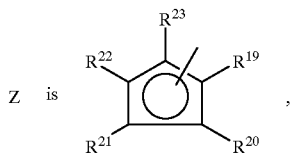, where the radicals $R^{19}$ to $R^{23}$ are identical or different and are each hydrogen, $C_1-C_{20}$-alkyl, 5- to 7-membered cycloalkyl which may in turn bear a $C_1-C_{10}$-alkyl group as substituent, $C_6-C_{15}$-aryl or arylalkyl, where adjacent radicals may together form cyclic groups having from 4 to 15 carbon atoms, or $Si(R^{24})_3$ where $R^{24}$ are identical or different and are each $C_1-C_{10}$-alkyl, $C_6-C_{15}$-aryl or $C_3-C_{10}$-cycloalkyl, or where the radicals $R^{16}$ and Z together form a group —[T($R^{25}$)($R^{26}$)]$_n$—E— where T can be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl n is 1, 2, 3 or 4, E is

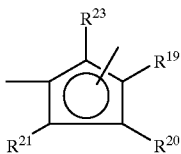

or A, where

A is —O—,

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl or alkylaryl, where p=1 for Be, Mg, Ca, Sr, Ba and p=2 for Li, Na, K, Rb, Cs.

Preferred compounds of the formula II are those in which $M^2$ is lithium, sodium and in particular magnesium. Furthermore, particular preference is given to those compounds of the formula II a)

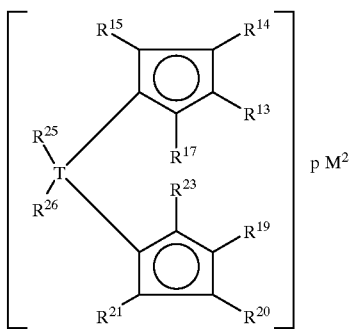

(II a)

in which $M^2$ is magnesium, $R^{17}$ and $R^{23}$ are substituents different from hydrogen, e.g. $C_1$–$C_{10}$-alkyl, such as methyl, ethyl, n-propyl, i-propyl, n-butyl, sec-butyl, tert-butyl, i-butyl or hexyl, also $C_6$–$C_{10}$-aryl, such as phenyl or trialkylsilyl, such as trimethylsilyl, $T(R^{25}R^{26})$ is bis-$C_1$–$C_{10}$-alkylsilyl or bis-$C_6$–$C_{10}$-arylsilyl, e.g. dimethylsilyl, diphenylsilyl, also 1,2-ethanediyl or methylene and the radicals $R^{13}$ to $R^{15}$ and $R^{19}$ to $R^{25}$ are as defined above and, in particular, form an indenyl-type ring system or a benzindenyl-type ring system.

Very particularly preferred compounds II are those which are described in the examples and additionally dimethylsilanediylbis(3-tert-butyl-5-methylcyclopentadienyl)magnesium diethylsilanediylbis(3-tert-butyl-5-methylcyclopentadienyl)magnesium dimethylsilanediylbis(3-tert-butyl-5-ethylcyclopentadienyl)magnesium dimethylsilanediylbis(3-tert-pentyl-5-methylcyclopentadienyl)magnesium dimethylsilanediylbis(2,4,7-trimethylindenyl)magnesium 1,2-ethanediylbis(1-{2,4,7-trimethylindenyl})magnesium dimethylsilanediylbis(1-indenyl)magnesium dimethylsilanediylbis(4,5,6,7-tetrahydro-1-indenyl)magnesium dimethylsilanediylbis(2-methylindenyl)magnesium phenyl(methyl)silanediylbis(2-methylindenyl)magnesium diphenylsilanediylbis(2-methylindenyl)magnesium dimethylsilanediylbis(2-methyl-4,5,6,7-tetrahydro-1-indenyl)magnesium dimethylsilanediylbis(2,4-dimethyl-6-isopropylindenyl)magnesium dimethylsilanediylbis(2-methyl-1-benzindenyl)magnesium dimethylsilanediylbis(2-ethyl-1-benzindenyl)magnesium dimethylsilanediylbis(2-propyl-1-benzindenyl)magnesium dimethylsilanediylbis(2-phenyl-1-benzindenyl)magnesium diphenylsilanediylbis(2-methyl-1-benzindenyl)magnesium phenylmethylsilanediylbis(2-methyl-1-benzindenyl)magnesium ethanediylbis(2-methyl-1-benzindenyl)magnesium dimethylsilanediylbis(2-methyl-1-tetrahydrobenzindenyl)magnesium dimethylsilanediylbis(2-methyl-4-isopropyl-1-indenyl)magnesium dimethylsilanediylbis(2-methyl-4-phenyl-1-indenyl)magnesium dimethylsilanediylbis(2-methyl-4-naphthyl-1-indenyl)magnesium dimethylsilanediylbis(2-methyl-4-{3,5-trifluoromethyl}phenyl-1-indenyl)magnesium dimethylsilanediylbis(2-ethyl-4-isopropyl-1-indenyl)magnesium dimethylsilanediylbis(2-ethyl-4-phenyl-1-indenyl)magnesium dimethylsilanediylbis(2-ethyl-4-naphthyl-1-indenyl)magnesium dimethylsilanediylbis(2-ethyl-4-{3,5-trifluoromethyl}phenyl-1-indenyl)magnesium ethanediylbis(2-methyl-4-phenyl-1-indenyl)magnesium ethanediylbis(2-methyl-4-naphthyl-1-indenyl)magnesium ethanediylbis(2-methyl-4-{3,5-di-(trifluoromethyl)}phenyl-1-indenyl)magnesium Such alkali metal or alkaline earth metal compounds II can be obtained by literature methods, for example by the, preferably stoichiometric, reaction of an organometallic compound or a hydride of the alkali or alkaline earth metal with the corresponding cyclopentadienyl-type hydrocarbons. Suitable organometallic compounds are, for example, n-butyllithium or di-n-butylmagnesium.

The reaction of the bridged or unbridged aromatic transition metal complexes I with the cyclopentadienyl derivatives of alkali or alkaline earth metals, preferably of the formula II or IIa), is usually carried out in an organic solvent or suspension medium, preferably in an ether such as diethyl ether, THF and at from −78 to 100° C., preferably at from 0 to 60° C. The molar ratio of the aromatic transition metal complex I to the cyclopentadienyl derivative of alkali or alkaline earth metals is usually in the range from 0.8:1 to 1:1.2, preferably 1:1.

The racemic metallocene complexes of the present invention are preferably those of the formula III

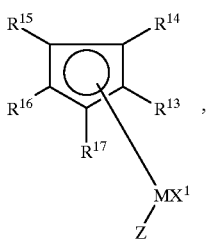 (III)

where the substituents and indices have the following meanings:

M is titanium, zirconium, hafnium, vanadium, niobium, tantalum, chromium, molybdenum, tungsten or an element of transition group III of the Periodic Table and the lanthanides,

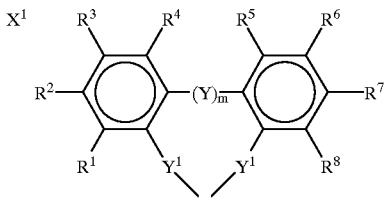

where:

$R^1$, $R^8$ are identical or different and are each fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms and the radicals mentioned may be fully or partially substituted by heteroatoms, Y, $Y^1$ are identical or different and are each

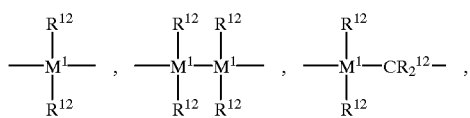

-continued

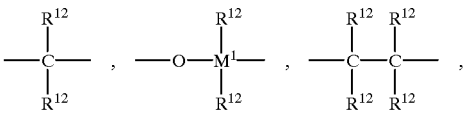

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2 or 3, or Y is non-bridging and is two radicals R' and R", where R' and R" are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms, $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where $R^{18}$ are identical or different and are each $C_1$–$C_{10}$-alkyl, $C_6$–$C_{15}$-aryl or $C_3$–$C_{10}$-cycloalkyl, Z is 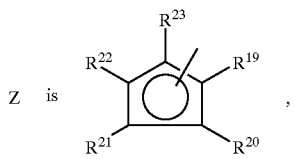, where the radicals $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where $R^{24}$ are identical or different and are each $C_1$–$C_{10}$-alkyl, $C_6$–$C_{15}$-aryl or $C_3$–$C_{10}$-cycloalkyl, or where the radicals $R^{16}$ and Z together form a group —[T($R^{25}$)($R^{26}$)]$_q$—E—, where T can be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl q is 1, 2, 3 or 4, E is

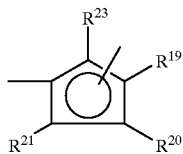

or A, where

A is —O—,

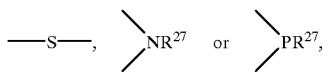

where
R²⁷ are identical or different and are each $C_1$–$C_{10}$-alkyl, $C_6$–$C_{15}$-aryl, $C_3$–$C_{10}$-cycloalkyl, alkylaryl or Si(R²⁸)₃
where
R²⁸ are identical or different and are each $C_1$–$C_{10}$-alkyl, $C_6$–$C_{15}$-aryl, $C_3$–$C_{10}$-cycloalkyl or alkylaryl.

Preferred compounds of the formula III are those in which M is titanium, hafnium or, in particular, zirconium. Furthermore, particular preference is given to bridged compounds of the formula III (ansa-metallocenes) in which R¹⁷ and R²³ are substituents different from hydrogen, e.g. $C_1$–$C_{10}$-alkyl, such as methyl, ethyl, n-propyl, i-propyl, n-butyl, sec-butyl, tert-butyl, i-butyl, hexyl, also $C_6$–$C_{10}$-aryl, such as phenyl or trialkylsilyl, such as trimethylsilyl, T(R²⁵R²⁶) is bis-$C_1$–$C_{10}$-alkylsilyl or bis-$C_6$–$C_{10}$-arylsilyl, e.g. dimethylsilyl, diphenylsilyl, also 1,2-ethanediyl, methylene and the radicals R¹³ to R¹⁵ and R¹⁹ to R²⁵ are as defined above and, in particular, form an indenyl-type ring system or a benzindenyl-type ring system.

Very particularly preferred compounds III are those which are described in the examples and additionally dimethylsilanediylbis(3-tert-butyl-5-methylcyclopentadienyl)[bis(6-tert-butyl-4-methylphenoxy)]zirconium
diethylsilanediylbis(3-tert-butyl-5-methylcyclopentadienyl)[bis(6-tert-butyl-4-methylphenoxy)]zirconium
dimethylsilanediylbis(3-tert-butyl-5-ethylcyclopentadienyl)[bis(6-tert-butyl-4-methylphenoxy)]zirconium
dimethylsilanediylbis(3-tert-pentyl-5-methylcyclopentadienyl)[bis(6-tert-butyl-4-methylphenoxy)]zirconium
dimethylsilanediylbis(2,4,7-trimethylindenyl)[bis(6-tert-butyl-4-methylphenoxy)]zirconium
1,2-ethanediylbis(1-{2,4,7-trimethylindenyl})[bis(6-tert-butyl-4-methylphenoxy)]zirconium
dimethylsilanediylbis(1-indenyl)[bis(6-tert-butyl-4-methylphenoxy)]zirconium
dimethylsilanediylbis(4,5,6,7-tetrahydro-1-indenyl)[bis(6-tert-butyl-4-methylphenoxy)]zirconium
dimethylsilanediylbis(2-methylindenyl)[bis(6-tert-butyl-4-methylphenoxy)]zirconium
phenyl(methyl)silanediylbis(2-methylindenyl)[bis(6-tert-butyl-4-methylphenoxy)]zirconium
diphenylsilanediylbis(2-methylindenyl)[bis(6-tert-butyl-4-methylphenoxy)]zirconium
dimethylsilanediylbis(2-methyl-4,5,6,7-tetrahydro-1-indenyl)[bis(6-tert-butyl-4-methylphenoxy)]zirconium
dimethylsilanediylbis(2,4-dimethyl-6-isopropylindenyl)[bis(6-tert-butyl-4-methylphenoxy)]zirconium
dimethylsilanediylbis(2-methyl-1-benzindenyl)[bis(6-tert-butyl-4-methylphenoxy)]zirconium
dimethylsilanediylbis(2-ethyl-1-benzindenyl)[bis(6-tert-butyl-4-methylphenoxy)]zirconium
dimethylsilanediylbis(2-propyl-1-benzindenyl)[bis(6-tert-butyl-4-methylphenoxy)]zirconium
dimethylsilanediylbis(2-phenyl-1-benzindenyl)[bis(6-tert-butyl-4-methylphenoxy)]zirconium
diphenylsilanediylbis(2-methyl-1-benzindenyl)[bis(6-tert-butyl-4-methylphenoxy)]zirconium
phenylmethylsilanediylbis(2-methyl-1-benzindenyl)[bis(6-tert-butyl-4-methylphenoxy)]zirconium
ethanediylbis(2-methyl-1-benzindenyl)[bis(6-tert-butyl-4-methylphenoxy)]zirconium
dimethylsilanediylbis(2-methyl-1-tetrahydrobenzindenyl)[bis(6-tert-butyl-4-methylphenoxy)]zirconium
dimethylsilanediylbis(2-methyl-4-isopropyl-1-indenyl)[bis(6-tert-butyl-4-methylphenoxy)]zirconium
dimethylsilanediylbis(2-methyl-4-phenyl-1-indenyl)[bis(6-tert-butyl-4-methylphenoxy)]zirconium
dimethylsilanediylbis(2-methyl-4-naphthyl-1-indenyl)[bis(6-tert-butyl-4-methylphenoxy)]zirconium
dimethylsilanediylbis(2-methyl-4-{3,5-trifluoromethyl}phenyl-1-indenyl)[bis(6-tert-butyl-4-methylphenoxy)]zirconium
dimethylsilanediylbis(2-ethyl-4-isopropyl-1-indenyl)[bis(6-tert-butyl-4-methylphenoxy)]zirconium
dimethylsilanediylbis(2-ethyl-4-phenyl-1-indenyl)[bis(6-tert-butyl-4-methylphenoxy)]zirconium
dimethylsilanediylbis(2-ethyl-4-naphthyl-1-indenyl)[bis(6-tert-butyl-4-methylphenoxy)]zirconium
dimethylsilanediylbis(2-ethyl-4-{3,5-trifluoromethyl}phenyl-1-indenyl)[bis(6-tert-butyl-4-methylphenoxy)]zirconium
ethanediylbis(2-methyl-4-phenyl-1-indenyl)[bis(6-tert-butyl-4-methylphenoxy)]zirconium
ethanediylbis(2-methyl-4-naphthyl-1-indenyl)[bis(6-tert-butyl-4-methylphenoxy)]zirconium
ethanediylbis(2-methyl-4-{3,5-di-(trifluoromethyl)}phenyl-1-indenyl)zirconium The racemic metallocene complexes, preferably those of the formula III, can generally be modified further.

In particular, a bridged bisphenoxide ligand X¹ in the complex III can, for example, be split off (replaced) and reused. Suitable replacement methods are reaction of the racemic metallocene complexes, preferably those of the formula III, with a Brönsted acid such as a hydrogen halide, ie. HF, HBr, HI, preferably HCl, which is generally employed as such or as a solution in water or an organic solvent such as diethyl ether, THF. This usually gives the dihalide analogous to the formula III (X=F, Cl, Br, I) and the bisphenol. Another well suited replacement method is reaction of the racemic metallocene complexes, preferably those of the formula III, with organoaluminum compounds such as tri-$C_1$–$C_{10}$-alkylaluminum, e.g. trimethylaluminum, triethylaluminum, tri-n-butylaluminum or tri-iso-butylaluminum. This generally gives, according to the present state of knowledge, the organo compound analogous to III (x=organic radical, e.g. $C_1$–$C_{10}$-alkyl, such as methyl, ethyl, n-butyl or i-butyl) and, for example, the organoaluminum binaphthoxide. An analogous method can also be employed if the ligand X¹ in the complex III consists of two unbridged phenoxide ligands.

In the cleavage reactions, the components are usually used in the stoichiometric ratio.

The stereochemistry of the metallocene complexes is generally retained during the cleavage reactions, ie. there is generally no conversion of the racemic form into the meso form of the metallocene complexes.

The process of the present invention makes it possible to obtain the racemic form of metallocene complexes very selectively. Bridged indenyl- or benzindenyl-type metallocenes which have a ligand different from hydrogen in the vicinity of the bridging unit (the 2 position) can be obtained particularly advantageously.

The racemic metallocene complexes of the present invention, in particular those of the formula III or their above-described derivatives which can be obtained, for example, by replacement of the phenoxide ligands, can be used as catalysts or in catalyst systems for the polymerization of olefinically unsaturated compounds such as ethylene, propylene, 1-butene, 1-hexene, 1-octene or styrene. Their use is particularly advantageous in the stereoselective polymerization of prochiral, olefinically unsaturated compounds such as propylene and styrene. Suitable catalysts or catalyst systems in which the racemic metallocene complexes of the present invention can function as "metallocene component" are usually obtained by means of compounds capable of forming metallocenium ions, as are described, for example, in EP-A-0 700 935, page 7, line 34 to page 8, line 21 and formulae (IV) and (V). Further compounds capable of forming metallocenium ions are aluminoxanes $(RAlO)_n$ such as methylaluminoxane.

The racemic metallocene complexes of the present invention, in particular those of the formula III or their above-described derivatives which can be obtained, for example, by splitting off the phenoxide ligands, can also be used as reagents or as catalysts or in catalyst systems in stereoselective, in particular organic, synthesis. As an example, mention may be made of the stereoselective reduction or stereoselective alkylation of C=C double bonds or C=O—, C=N double bonds.

EXAMPLES

ABBREVIATIONS AND ACRONYMS

Me=methyl, tBu=tert-butyl, iPr=iso-propyl

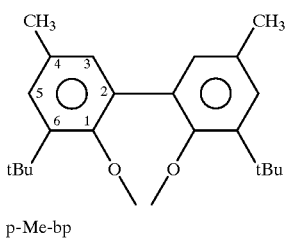

p-Me-bp

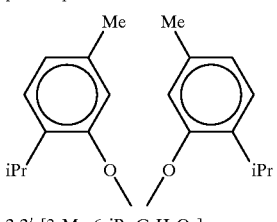

2,2'-[3-Me-6-iPr-C₆H₂O₂]

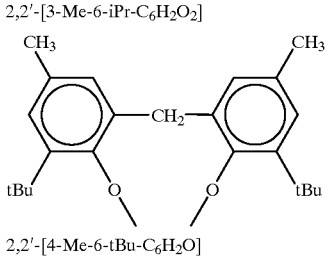

2,2'-[4-Me-6-tBu-C₆H₂O]

-continued

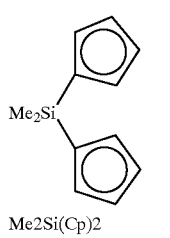

Me2Si(Cp)2

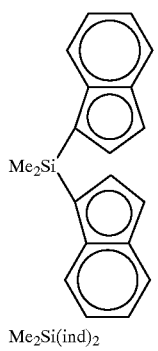

Me2Si(ind)2

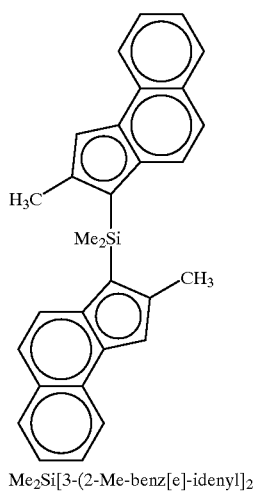

Me2Si[3-(2-Me-benz[e]-idenyl]2

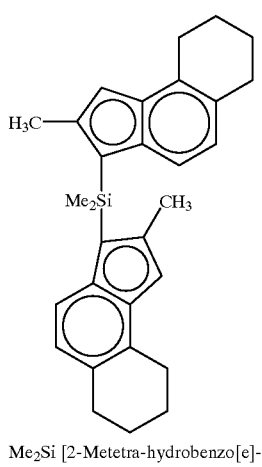

Me2Si [2-Metetra-hydrobenzo[e]-inden-3-yl]

-continued

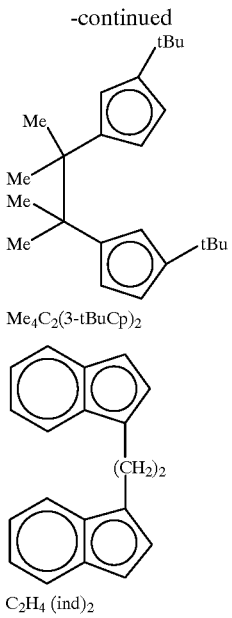

Me₄C₂(3-tBuCp)₂

C₂H₄ (ind)₂

Example A
Preparation of Dichlorobis(6-t-butyl-4-methylphenoxy) zirconium-(THF)₂[p-Me-bpZrCl₂(THF)₂]

0.483 g (0.02 mol) of NaH was added a little at a time at room temperature while stirring to a solution of 3.27 g (0.01 mol) of 2,2'-dihydroxy-3,3'-di-t-butyl-5,5'-dimethylbiphenyl in 150 ml of THF, the mixture was subsequently stirred for one hour at room temperature and the suspension was then refluxed for 24 hours. After cooling the clear, slightly orange solution, 3.8 g (0.01 mol) of ZrCl₄× 2THF were added a little at a time while stirring and the suspension was again refluxed for 24 hours. The NaCl formed was filtered off and the solvent was removed under reduced pressure. 100 ml of ether were added to the residue. After a short time, a white solid precipitated from the initially clear solution. To complete the crystallization, the solution was cooled to −30° C. The precipitate was filtered off and washed with a little cold ether. This gave 4.59 g (73% of theory) of dichlorobis(6-t-butyl-4-methylphenoxy) zirconium×2THF: [p-Me-bp]ZrCl₂×2THF.

¹H-NMR: (C₆D₆, 250 Mhz): 7.26 (d, 2H, C₆H₂), 7.04 (d, 2H, C₆H₂), 4.06 (b, 8H, THF), 2.21 (s, 6H, Me), 1.74 (s, 18H, t-Bu), 1.05 (b, 8H, THF)

Example 1
Preparation of Rac-C₂H₄(ind)₂Zr(p-Me-bp)
a) Preparation of C₂H₄(ind)₂Mg(THF)₂

6.3 ml of dibutyl magnesium in heptane (6.3 mmol, 1 M Bu₂Mg solution) were added at room temperature to a solution of 1.49 g (5.77 mmol) of C₂H₄(indH)₂ in 150 ml of heptane. The solution was refluxed for 5 hours. This resulted in formation of a yellowish precipitate. The suspension was cooled to −30° C., the precipitate was filtered off, washed with a little heptane and dried under reduced pressure. The crude product was taken up in a little THF and covered with heptane. The C₂H₄(ind)₂Mg(THF)₂ was obtained in the form of pale violet needles. The yield was 1.86 g (76% of theory)

b) Complexation
0.459 g (1.08 mmol) of C₂H₄(ind)₂Mg(THF)₂ and 0.679 g (1.08 mmol) of p-Me-bpZrCl₂(THF)₂ were mixed dry. While stirring, 50 ml of toluene were added and the suspension was stirred for two days at room temperature. During this time, the solution became increasingly yellow-orange and became turbid. The precipitate was filtered off, the toluene was removed from the filtrate under reduced pressure and the residue was taken up in 100 ml of pentane. The slightly turbid solution was filtered through kieselguhr and the pentane was removed under reduced pressure. This gave 0.495 g (68% of theory) of rac-C₂H₄(ind)₂Zr(p-Me-bp).

¹H-NMR: (C₆D₆, 250 Mhz): 7.40 (d, 2H, ind-C₆H₄), 7.21 (d, 2H, C₆H₂), 6.9 (m, 6H, ind-C₆H₄), 6.77 (d, 2H, C₆H₂), 6.00 (d, 2H, ind-C₃H₂), 5.76 (d, 2H, ind-C₉H₂), 3.29 (m, 4H, C₂H₄), 2.18 (s, 6H, Me), 1.36 (s, 18H, t-Bu).

Example 2
Preparation of Rac-Me₂Si(2-Me-Tetrahydrobenzo[e]inden-3-yl)₂-Zr((p-Me-bp)
a) Preparation of Me₂Si(2-Me-Tetrahydrobenzo[e]inden-3-yl)₂-Mg(THF)₂

2.5 ml (2.5 mmol) of a 1 M dibutylmagnesium solution in heptane were added to a solution of 1 g (2.35 mmol) of rac-Me₂Si(2-Me-tetrahydrobenzo[e]inden-3-yl)2Mg in 100 ml of heptane. The solution was refluxed for 6 hours. After cooling to room temperature, 0.4 ml of THF was added. After a few days at room temperature, yellow-green needles of Me₂Si(2-Me-tetrahydrobenzo[e]inden-3-yl)₂Mg (THF)₂.0.5(C₇H₁₆) were isolated by decantation, washed with a little heptane and dried under reduced pressure. This gave 0.57 g (38% of theory) of the desired product.

¹H-NMR: (CH₂Cl₂, 600 Mhz): 7.53 (d, 2H, C₆H₂), 6.55 (d, 2H, C₆H₂), 6.28 (s, 2H, C₅H₁), 3.2–2.4 (m), 2.2–1.5 (m), 0.65 (d, 6H, Me₂Si)

b) Preparation of Rac-Me₂Si(2-Me-Tetrahydrobenzo[e]inden-3-yl)₂-Zr(p-Me-bp)

500 mg (0.85 mmol) of Me₂Si(2-Me-tetrahydrobenzo[e]inden-3-yl)₂-Mg(THF)₂ and 556 mg (0.85 mmol) of p-Me-bpZrCl₂(THF)₂ were mixed dry. While stirring, 60 ml of toluene were added and the suspension was stirred for two days at room temperature. During this time, the solution became increasingly yellow and became turbid. The precipitate was filtered off, the toluene was removed from the filtrate under reduced pressure and the residue was taken up in 100 ml of pentane. The slightly turbid solution was filtered and the pentane was removed under reduced pressure. This gave 0.498 g (70% of theory) of rac-Me₂Si(2-Me-tetrahydrobenzo[e]inden-3-yl)₂Zr(p-Me-bp).

¹H-NMR: (₆D₆, 250 Mhz): 7.46 (d, 2H, ind-C₆H₂), 7.22 (d, 2H, C₆H₂), 6.73 (d, 2H, C₆H₂), 6.52 (d, 2H, ind-C₆H₂), 6.09 (s, 2H, C₅H₁), 2.46 (s, 6H, ind-Me), 2.21 (s, 6H, Me), 138 (s, 18H, t-Bu), 0.96 (s, 6H, Me₂Si)

Example 3
Preparation of Me₂SiCp₂Mg(THF)₂

11.21 ml (12.20 mmol) of a 1.08 m dibutylmagnesium solution in heptane were added to a solution of 2.28 g (12.10 mmol) of Me₂Si(CPH)₂ in 60 ml of heptane. This resulted in the solution becoming turbid owing to a white precipitate. The solution was refluxed for 5 hours. At room temperature, 3 ml (37 mmol) of THF were added. The solution was stirred for 1 hour at room temperature, evaporated to about 30 ml in a high vacuum and stored at −30° C. in a freezer. After a few days, the white precipitate was filtered off, washed with a little heptane and dried under reduced pressure. This gave 3.35 g (78%) of Me₂SiCp₂Mg(THF)₂.

¹H-NMR chemical shifts in ppm (CD₂Cl₂, internal standard TMS, 298 K, 250 MHz)

| Assignment | |
|---|---|
| 6.21 tp | $C_5H_4$ |
| 6.09 sb | $C_5H_4$ |
| 3.64 m | THF |
| 1.85 m | THF |
| 0.54 s | $(CH_3)_2Si$ |

Example 4
Preparation of $Me_4C_2(3-{}^tBu-Cp)_2Mg(THF)_2$ 23 ml (23 mmol) of a 1 M dibutylmagnesium solution in heptane were added to a solution of 6.78 g (20.76 mmol) of $Me_4C_2(3-tBu-CpH)_2$ in 200 ml of heptane. The solution was refluxed for 5 hours during which the evolution of butane could be observed. 4 ml of THF were added to the slightly yellowish solution and the mixture was stirred for 1 hour at room temperature, evaporated to a quarter of its value and cooled to −30° C. After a few days, colorless crystals had formed. These were separated off by decantation, washed with a little heptane and dried under reduced pressure. This gave 6.83 g (78%) of $Me_4C_2(3-{}^tBu-Cp)_2Mg(THF)$. Further evaporation of the mother liquor and cooling to −30° C. gave, after the same work-up, a further 0.35 g (4%) of $Me_4C_2(3-{}^tBu-Cp)_2Mg(THF)$.

$^1$H-NMR chemical shifts in ppm ($CD_2Cl_2$, internal standard TMS, 298 K, 600 MHz)

| | Assignment | |
|---|---|---|
| 5.96 (t$^p$, 1H) | $C_5H_3$ | (H2) |
| 5.56 (t$^p$, 1H) | $C_5H_3$ | (H4) |
| 5.47 (t$^p$, 1H) | $C_5H_3$ | (H5) |
| 1.54 (s, 6H) | $C_2(CH_3)_2(CH_31)$ | |
| 1.40 (s, 6H) | $C_2(CH_3)_2(CH_32)$ | |
| 1.16 (s, 18H) | $C(CH_3)_3$ | |

Example 5
Preparation of $Me_2Si(ind)_2Mg(THF)_2$ 37 ml (37 mmol) of a 1 M dibutylmagnesium solution in heptane were added to a solution of 10.54 g (36.54 mmol) of $Me_2Si(indH)_2$ in 150 ml of heptane. The solution was refluxed for 8 hours while stirring vigorously. Small amounts of a precipitate were formed. 30 ml of THF (0.37 mol) were then added at room temperature while stirring vigorously. A whitish pink solid immediately precipitated. This was filtered off, washed with a little heptane and dried in a high vacuum. This gave 9.98 g (61%) of $Me_2Si(ind)_2Mg(THF)_2$. The filtrate was evaporated to a much smaller volume in a high vacuum and the solution was stored at −30° C. in a freezer. After a few days, a further 1.85 g (11%) of $Me_2Si(ind)_2Mg(THF)_2$ were obtained by an identical work-up. Total yield: 72%

$^1$H-NMR chemical shifts in ppm ($CD_2Cl_2$, internal standard TMS, 298 K, 250 MHz)

| Assignment | |
|---|---|
| 7.96 (d, 2H) $^3$J (7.9 Hz) | $C_6H_4$ |
| 7.52 (d, 2H) $^3$J (7.9 Hz) | $C_6H_4$ |
| 6.98 (d, 2H) $^3$J (3.3 Hz) | $C_5H_2$ |
| 6.93 (t$^p$, 2H) | $C_6H_4$ |

-continued

| Assignment | |
|---|---|
| 6.83 (t$^p$, 2H) | $C_6H_4$ |
| 6.53 (d, 2H) $^3$J (3.1 Hz) | $C_5H_2$ |
| 3.03 (d, 8H) | THF |
| 1.51 (b, 8H) | THF |
| 0.94 (s, 6H) | $(CH_3)_2Si$ |

Example 6
Preparation of $Me_2Si(3-{}^tBu-Cp)_2Mg(THF)_2$ 19.65 ml (19.65 mmol) of a 1 M dibutylmagnesium solution in heptane were added to a solution of 5.37 g (17.86 mmol) of $Me_2Si(3-{}^tBu-CpH)_2$ in 200 ml of heptane. The reaction solution was refluxed for 5 hours during which the evolution of butane could be observed. The clear solution was evaporated to about one third of its volume. 3 ml (36.86 mmol) of THF were added at room temperature and the solution was cooled to −30° C. After a few days, some colorless crystals and some amorphous precipitate were formed. Both were isolated by decantation, washed with a little heptane and dried in a high vacuum. This gave 5.1 g (61%) of $Me_2Si(3-{}^tBu-Cp)_2Mg(THF)_2$. Further evaporation of the mother liquor and cooling to −30° C. gave, after identical isolation, a further 2.0 g (24%) of $Me_2Si(3-{}^t-Bu-Cp)_2Mg(THF)_2$.

$^1$H-NMR chemical shifts in ppm ($d^8$-THF, internal standard TMS, 298 K, 600 MHz)

| | Assignment | |
|---|---|---|
| 6.14 (s, 2H) | $C_5H_3$ | (H4) |
| 6.00 (s, 2H) | $C_5H_3$ | (H2) |
| 5.67 (s, 2H) | $C_5H_3$ | (H5) |
| 1.16 (s, 18H) | $(CH_3)_3C$ | |
| 0.37 (b, 6H) | $(CH_3)_2Si$ | |

Example 7
Preparation of $Me_2Si(3-(2-Me-benz[e]indenyl)_2Mg(THF)_2$ 3 ml (3 mmol) of a 1 M dibutylmagnesium solution were added at room temperature to a suspension of 1.09 g (2.61 mmol) of $Me_2Si(3-(3H-2-Me-benz[e]indenyl)_2$ in 80 ml of heptane. The suspension was heated to boiling under reflux. Shortly before the boiling point, the solution was clear. The solution became turbid after about 30 minutes as a result of precipitated product and the evolution of butane could be observed. After boiling for 12 hours, 6 ml (74 mmol) of THF were added at room temperature to the yellow suspension. The solid became brilliant yellow. After stirring for 1 hour at room temperature, the suspension was evaporated to about 20 ml in a high vacuum, the precipitate was filtered off, washed with a little heptane and dried in a high vacuum. This gave 1.29 g (85%) of $Me_2Si(3-(2-Me-benz[e]indenyl)_2Mg(THF)_2$.

$^1$H-NMR chemical shifts in ppm ($C_6D_6$, internal standard TMS, 298 K, 250 MHz)

| Assignment | |
|---|---|
| 8.45 (d, 2H) | $C_6H_4$ or $C_6H_2$ |
| 8.34 (d, 2H) | $C_6H_4$ or $C_6H_2$ |

-continued

| | Assignment |
|---|---|
| 8.23 (d, 2H) | $C_6H_4$ or $C_6H_2$ |
| 7.82 (d, 2H) | $C_6H_4$ or $C_6H_2$ |
| 7.42 (t$^p$, 2H) | $C_6H_4$ |
| 7.22 (t$^p$, $C_6D_6$) | $C_6H_4$ |
| 7.14 (s, 2H) | $C_5H$ |
| 2.95 (s, 6H) | $CH_3$ |
| 2.79 (b, 8H) | THF |
| 1.10 (s, 6H) | $(CH_3)_2Si$ |
| 1.07 (b, 8H) | THF |

Example 8
Preparation of Rac-$C_2H_4$(ind)$_2$Zr-(2,2'-(3-Me-6-iPr-$C_6H_2O)_2$)

0.172 g (0.40 mmol) of 2,2'(3-$^i$Pr-5-Me-$C_6H_2O)_2$Zr(THF)$_2$ and 0.245 g (0.40 mmol) of $C_2H_4$(ind)$_2$Mg(THF)$_2$ were mixed dry and dissolved in 20 ml of toluene. The solution became increasingly yellow and became turbid. After stirring at room temperature for 3 hours, the solvent was removed in a high vacuum and the residue was taken up in hexane. The MgCl$_2$(THF)$_2$ was filtered off and washed with hexane. The solvent was removed in a high vacuum and the residue was taken up in 3 ml of toluene. After a few days at room temperature, pale yellow crystals were formed. These were isolated by decantation and dried in a high vacuum. This gave 0.110 g (41%) of $C_2H_4$(ind)$_2$Zr-(2,2'-(3-Me-6-iPr-$C_6H_2O)_2$).

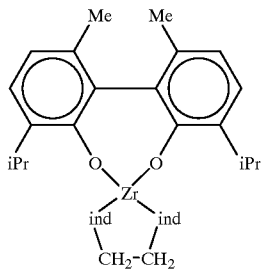

$^1$H-NMR chemical shifts in ppm ($C_6D_6$, internal standard TMS, 298 K, 600 MHz)

| | Assignment |
|---|---|
| 7.36 (d, 2H) $^3$J (8.5 Hz) | $C_6H_4$ (H7) |
| 7.15 (under $C_6D_6$ signal) | $C_6H_4$ (H4) |
| 6.94 (t$^p$, 2H) | $C_6H_4$ (H6) |
| 6.87 (t$^p$, 2H) | $C_6H_4$ (H5) |
| 6.80 (d, 2H) $^3$J (7.6 Hz) | $C_6H_2$ (H5) |
| 6.71 (d, 2H) $^3$J (8.5 Hz) | $C_6H_4$ (H4) |
| 5.93 (d, 2H) $^3$J (3.1 Hz) | $C_5H_2$ (H2) |
| 5.53 (d, 2H) $^3$J (3.0 Hz) | $C_5H_2$ (H3) |
| 3.23 (s, 6H) | $C_2H_4$ |
| 2.82 (sp, 2H) $^3$J (6.8 Hz) | $(CH_3)_2CH$ |
| 1.94 (s, 6H) | $CH_3$ |
| 1.40 (d, 6H) $^3$J (7.1 Hz) | $(CH_3)_2CH$ |
| 1.16 (d, 6H) $^3$J (6.6 Hz) | $(CH_3)_2CH$ |

Example 9
Preparation of 2,2'-$CH_2$-(4-Me-6-$^t$Bu-$C_6H_2O)_2$ZrCl$_2$(THF)$_2$ 1.44 g (60 mmol) of NaH were added a little at a time to a solution of 10.2 g (30 mmol) of 2,2'-$CH_2$-(4-Me-6-$^t$BUC$_6H_2$OH)$_2$ in 100 ml of THF. The suspension was subsequently refluxed for 24 hours. At room temperature, 11.3 g (30 mmol) of ZrCl$_4$(THF$_2$) were then added to the clear, orange solution and the solution was refluxed for 12 hours. The NaCl formed was filtered off, washed with THF and the solvent was removed from the filtrate in a high vacuum. 50 ml of ether were added to the foamed solid. After a short time, a white solid precipitated from the initially clear solution. This was separated off by decantation, washed with a little ether and dried in a high vacuum. This gave 12.38 g (64%) of 2,2'-$CH_2$-(4-Me-6-$^t$Bu-$C_6H_2O)_2$ZrCl$_2$(THF)$_2$. The mother liquor and the washing solution were combined, evaporated to a much smaller volume in a high vacuum and stored at $-30°$ C. in a freezer. After a few days, the crystalline precipitate was isolated in the same way. This gave a further 2.11 g (11%) of 2,2'-$CH_2$-(4-Me-6-$^t$Bu-$C_6H_2O)_2$ZrCl$_2$(THF)$_2$. Total yield: 75%

$^1$H-NMR chemical shifts in ppm ($CD_2Cl_2$, internal standard TMS, 298 K, 250 MHz)

| | | Assignment |
|---|---|---|
| 7.16 (d, 2H) $^4$J (1.8 Hz) | 7.27 | $C_6H_2$ |
| 6.96 (d, 2H) $^4$J (1.9 Hz) | 7.05 | $C_6H_2$ |
| 5.3 (b,1H) | | $CH_2$ |
| 4.45 (m, 8H) | | THF |
| 3.33 (d, 1H) $^3$J (1.9 Hz) | | $CH_2$ |
| 2.31 (s, 6H) | 2.34 | $CH_3$ |
| 2.04 (m, 8H) | | THF |
| 1.49 (s, 18H) | 1.56 | $(CH_3)_3C$ |

Example 10
Preparation of Rac-Me$_2$SiCp$_2$Zr(2,2'-$CH_2$-(4-Me-6-$^t$BuC$_6H_2O)_2$)

0.374 g (1.05 mmol) of Me$_2$SiCp$_2$Mg(THF)$_2$ and 0.680 g (1.05 mmol) of 2,2'-$CH_2$-(4-Me-6-$^t$BuC$_6H_2O)_2$ZrCl$_2$(THF)$_2$ were mixed dry and dissolved in 30 ml of toluene. The solution was stirred for 4 days at room temperature, during which time it became yellow and turbid. The solvent was removed in a high vacuum and the residue was taken up in heptane. The MgCl$_2$(THF)$_2$ was filtered off, washed with heptane and the filtrate was evaporated to about 30 ml. After a few days at room temperature, yellow crystals formed. These were isolated by decantation and dried in a high vacuum. This gave 0.311 g (48%) of Me$_2$SiCp$_2$Zr(2,2'-$CH_2$-(4-Me-6-$^t$BuC$_6H_2O)_2$). Evaporation of the mother liquor and cooling to $-30°$ C. gave, after a few days, a further 0.154 g (24%) of Me$_2$SiCp$_2$Zr(2,2'-$CH_2$-(4-Me-6-$^t$BuC$_6H_2O)_2$) by means of an identical work-up. Total yield: 72%

$^1$H-NMR chemical shifts in ppm ($CD_2Cl_2$, internal standard TMS, 298 K, 600 MHz)

| | Assignment |
|---|---|
| 7.09 (d, 2H) $^4$J (1.3 Hz) | $C_6H_2$ (H6) |
| 6.92 (d, 2H) $^4$J (1.5 Hz) | $C_6H_2$ (H4) |
| 6.85 (t$^p$, 2H) | $C_5H_4$ |
| 6.17 (t$^p$, 2H) | $C_5H_4$ |
| 6.01 (t$^p$, 2H) | $C_5H_4$ |
| 5.95 (t$^p$, 2H) | $C_5H_4$ |
| 4.21 (d, 1H) $^3$J (13.8 Hz) | $CH_2$ |
| 3.11 (d, 1H) $^3$J (13.8 Hz) | $CH_2$ |
| 2.26 (s, 6H) | $CH_3$ |
| 1.41 (s, 18H) | $(CH_3)_3CH$ |
| 0.811 (s, 6H) | $(CH_3)_2Si$ |

Example 11
Preparation of Rac-Me$_2$Si(3-(2-Me-benz[e]indenyl)$_2$Zr(2,2'-(3-$^t$Bu-5-Me-C$_6$H$_2$O)$_2$)

17 mg (0.029 mmol) of Me$_2$Si(3-(2-Me-benz[e]indenyl)$_2$Mg(THF)$_2$ and 18.3 mg (0.0291 mmol) of 2,2'-(3-$^t$Bu-5-Me-C$_6$H$_2$O)$_2$ZrCl$_2$(THF)$_2$ were mixed dry in an NMR tube and dissolved in 0.5 ml of C$_6$D$_6$. After 6 days at room temperature, the solution is yellow and a new white precipitate has formed. An $^1$H-NMR spectrum was recorded.

$^1$H-NMR chemical shifts in ppm (C$_6$D$_6$, internal standard TMS, 298 K, 250 MHz)

|  | Assignment |
|---|---|
| 8.63 (d) | C$_6$H$_4$ or C$_6$H$_2$ |
| 7.97 (d) | C$_6$H$_4$ or C$_6$H$_2$ |
| 7.78 (m) | C$_6$H$_4$ or C$_6$H$_2$ |
| 7.82 | C$_6$H$_4$ or C$_6$H$_2$ |
| 7.52 (m) | C$_6$H$_4$ or C$_6$H$_2$ |
| 7.35–7.03 (m) | C$_6$H$_4$ or C$_6$H$_2$, C$_6$H$_2$ (phenoxy ligand) |
| 6.97 (d) | C$_6$H$_2$ (phenoxy ligand) |
| 6.84 (s) | C$_5$H |
| 3.43 (sb) | THF (free) |
| 3.25 (s) | CH$_3$ |
| 2.27 (s) | CH$_3$ (phenoxy ligand) |
| 1.45 (m) | THF (free) |
| 1.23 (s) | (CH$_3$)$_3$C |
| 1.16 (s) | (CH$_3$)$_2$Si |

Example 12
Preparation of Cl$_2$Zr(O-2,6-Me$_2$C$_6$H$_3$)$_2$(THF)$_2$ 5.21 g (13.81 mmol) of ZrCl$_4$(THF)$_2$ were suspended in 150 ml of toluene. At 0° C., 16 g (82.3 mmol) of Me$_3$SiO-2,6-(CH$_3$)$_2$-C$_6$H$_3$ were added thereto and the suspension was subsequently refluxed for 12 hours. The solvent was taken off and the residue was taken up in 80 ml of THF. This solution was covered with a layer of hexane. After some days at room temperature, colorless crystals were formed and these were isolated by decantation and dried in a high vacuum. This gave 1.82 g (3.31 mmol) of Cl$_2$Zr(O-2,6-Me$_2$C$_6$H$_3$)$_2$(THF)$_2$. Further concentration of the mother liquor and cooling to −30° C. gave, after identical isolation, a further 2.20 g (4.01 mmol) of Cl$_2$Zr(O-2,6-Me$_2$C$_6$H$_3$)$_2$(THF)$_2$.

Total yield: 4.02 g (7.32 mmol, 53%) of Cl$_2$Zr(O-2,6-Me$_2$C$_6$H$_3$)$_2$(THF)$_2$ Preparation of rac-C$_2$H$_4$(ind)$_2$Zr(O-2,6-Me$_2$C$_6$H$_3$)$_2$ 15.7 mg (0.028 mmol) of Cl$_2$Zr(O-2,6-Me$_2$C$_6$H$_3$)$_2$(THF)$_2$ and 12.1 mg (0.028 mmol) of C$_2$H$_4$(ind)$_2$Mg(THF)$_2$ were mixed dry in an NMR tube and dissolved in 0.5 ml of C$_6$D$_6$. After 24 hours at room temperature, the solution had turned yellow and had become turbid due to precipitated MgCl$_2$(THF)$_2$. A $^1$H-NMR spectrum was recorded and this found that only the racemic form of C$_2$H$_4$(ind)$_2$Zr-(O-2,4-Me$_2$C$_6$H$_5$)$_2$ had been formed.

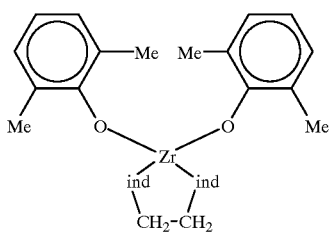

$^1$H-NMR chemical shifts in ppm (C$_6$D$_6$, internal standard TMS, 298 K, 250 MHz)

|  | Assignment |
|---|---|
| 7.46 (d, 2H) | C$_6$H$_4$ |
| 7.02 (d, 2H) | C$_6$H$_4$ |
| 6.92 (d, 4H) | C$_6$H$_3$ |
| 6.82 (m, 4H) | C$_6$H$_3$ or C$_6$H$_4$ |
| 6.44 (tp, 2H) | C$_5$H$_4$ |
| 6.14 (d, 2H) | C$_5$H$_2$ |
| 5.94 (d, 2H) | C$_5$H$_2$ |
| 3.52 (m, 2H) | C$_2$H$_4$ |
| 3.17 (m, 2H) | C$_2$H$_4$ |
| 1.97 (s, 6H) | CH$_3$ |

Example 13
Preparation of Rac-Me$_2$Si(ind)$_2$Zr(O-2,6-Me$_2$C$_6$H$_3$)$_2$ 25 mg (0.045 mmol) of Me$_2$Si(ind)$_2$Mg(THF)$_2$ and 20.5 mg (0.045 mmol) of Cl$_2$Zr(O-2,6-Me$_2$C$_6$H$_3$)$_2$(THF)$_2$ were mixed dry in an NMR tube and dissolved in 0.5 ml of C$_6$D$_6$. After 24 hours at room temperature, the solution had turned yellow and had become turbid due to precipitated MgCl$_2$(THF)$_2$. A $^1$H-NMR spectrum was recorded and this showed that only the racemic form of Me$_2$Si(ind)$_2$Zr(O-2,6-Me$_2$C$_6$H$_3$)$_2$ had been formed.

$^1$H-NMR chemical shifts in ppm (C$_6$D$_6$, internal standard TMS, 298 K, 250 MHZ).

|  | Assignment |
|---|---|
| 7.57 (d, 2H) | C$_6$H$_4$ |
| 7.20 (d, 2H) | C$_6$H$_4$ |
| 6.96–6.70 (m) | C$_6$H$_3$ or C$_6$H$_4$ |
| 6.47 (s, 4H) | C$_5$H$_2$ |
| 6.44 (tp, 2H) | C$_6$H$_4$ |
| 2.37–1.97 (m, 6H) | CH$_3$ |
| 0.81 (s, 6H) | Me$_2$Si |

We claim:

1. A process for preparing racemic metallocene complexes by reacting bridged or unbridged aromatic transition metal complexes of the formula I

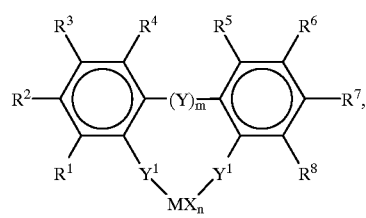

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen C$_1$–C$_{10}$-alkyl, C$_6$–C$_{15}$-aryl, alkylaryl having from 1 to 10 carbon atoms in the alkyl radical and from 6 to 20 carbon atoms in the aryl radical, —OR$^{10}$ or —NR$^{10}$R$^{11}$, n is an integer from 1 to 4, where n corresponds to the valence of M minus 2, $R^1$, $R^8$ are identical or different and are each fluorine, chlorine, bromine, iodine, $C_1$–$C_{20}$-alkyl, 3- to 8-membered cycloalkyl which in turn may bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, $R^2$ to $R^7$ are identical or different and are each hydrogen, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms, and the radicals mentioned can be fully or partially substituted by heteroatoms, $R^{10}$, $R^{11}$ are $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, $Y^1$ are identical or different and are each

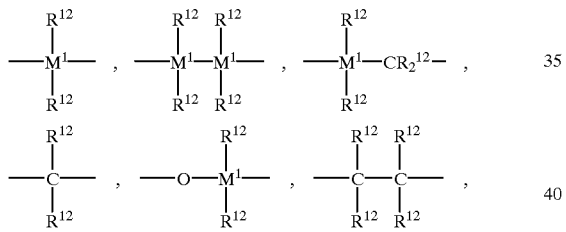

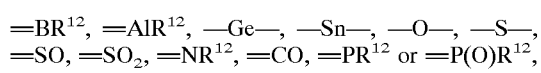

where
$R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2 or 3, or Y is non-bridging and is two radicals R' and R", where R' and R" are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms, with cyclopentadienyl derivatives of alkali metals or alkaline earth metals and, if desired, subsequently replacing the bridged aromatic ligand or the two unbridged aromatic ligands.

2. A process as claimed in claim 1, wherein $R^1$ and $R^8$ in formula I are bulky substituents.

3. A process as claimed in claim 1, wherein m in formula I is 0.

4. A process as claimed in claim 1, wherein $Y^1$ are identical and are each oxygen.

5. A process as claimed in claim 1, wherein cyclopentadienyl derivatives of magnesium are used.

6. A racemic metallocene complex of the formula III (III)

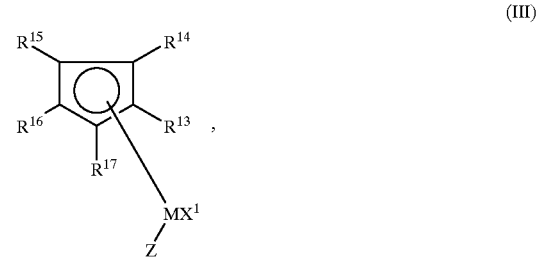

where the substituents and indices have the following meanings:

M is titanium, zirconium, hafnium, vanadium, niobium, tantalum, chromium, molybdenum, tungsten or an element of transition group III of the Periodic Table and the lanthanides,

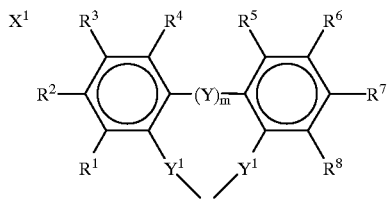

where:
$R^1$, $R^8$ are identical or different and are each fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, and adjacent radicals $R^2$ to $R^7$ may form saturated, partially saturated or unsaturated cyclic groups having from 4 to 15 carbon atoms and the radicals mentioned may be fully or partially substituted by heteroatoms, Y, $Y^1$ are identical or different and are each

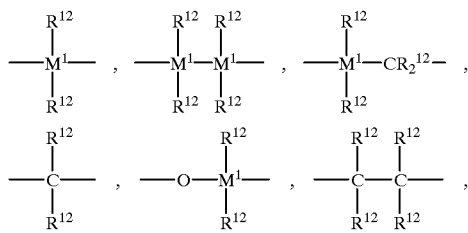

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2 or 3, or Y is non-bridging and is two radicals R' and R", where R' and R" are identical or different and are each hydrogen, fluorine, chlorine, bromine, iodine, $C_1$–$C_{20}$-alkyl, 3- to 8-membered cycloalkyl which in turn may bear a $C_1$–$C_{10}$-alkyl radical as substituent, $C_6$–$C_{15}$-aryl, alkylaryl having from 1 to 10 carbon atoms in the alkyl radical and from 6 to 20 carbon atoms in the aryl radical, arylalkyl having from 1 to 10 carbon atoms in the alkyl radical and from 6 to 20 carbon atoms in the aryl radical, $Si(R^9)_3$ where $R^9$ are identical or different and are each $C_1$–$C_{20}$-alkyl, $C_3$–$C_{10}$-cycloalkyl, $C_6$–$C_{15}$-aryl, or together with adjacent radicals $R^4$ or $R^5$ form saturated, partially saturated or unsaturated cyclic groups having from 4 to 15 carbon atoms, and the radicals mentioned can be fully or partially substituted by heteroatoms, $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where $R^{18}$ are identical or different and are each $C_1$–$C_{10}$-alkyl, $C_6$–$C_{15}$-aryl or $C_3$–$C_{10}$-cycloalkyl, Z is 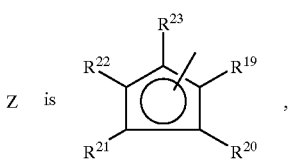

where the radicals $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where $R^{24}$ are identical or different and are each $C_1$–$C_{10}$-alkyl, $C_6$–$C_{15}$-aryl or $C_3$–$C_{10}$-cycloalkyl, or where the radicals $R^{16}$ and Z together form a group —$[T(R^{25})(R^{26})]_q$—E—, where T can be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl q is 1, 2, 3 or 4, E is

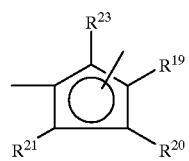

or A, where

A is —O—,

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl or alkylaryl.

7. A racemic metallocene complex as claimed in claim 6, wherein $R^{17}$ and $R^{23}$ are not hydrogen if $R^{16}$ and Z together form a group —$[T(R^{25})(R^{20})]_q$—E—.

8. A catalyst for the polymerization of olefinically unsaturated compounds or for stereoselective synthesis comprising racemic metallocene complexes of the formula III as claimed in claim 6.

9. A process for polymerizing olefinically unsaturated compounds comprising polymerization in the presence of racemic metallocene complexes of the formula III as claimed in claim 6 as a catalyst or as a constituent of a catalyst system.

10. A process for stereoselective synthesis comprising synthesis in the presence of racemic metallocene complexes of the formula III as claimed in claim 6 as a catalyst or as a constituent of a catalyst system.

* * * * *

UNITED STATES PATENT AND TRADEMARK OFFICE
CERTIFICATE OF CORRECTION

PATENT NO.    : 6,262,286 B1
DATED         : July 17, 2001
INVENTOR(S)   : Gregorius et al.

It is certified that error appears in the above-identified patent and that said Letters Patent is hereby corrected as shown below:

<u>Title page,</u>
Item [73], Assignee information should read as follows:
-- Targor GmbH,
   Mainz (DE) --

Signed and Sealed this

Twenty-third Day of April, 2002

*Attest:*

JAMES E. ROGAN
*Attesting Officer*   *Director of the United States Patent and Trademark Office*